United States Patent
Day et al.

[11] 3,946,256
[45] Mar. 23, 1976

[54] SYSTEM FOR GENERATING OR SENSING TRANSVERSE ELASTIC BULK WAVES IN SOLIDS

[75] Inventors: Clifford K. Day, Richland, Wash.; George G. Koerber, Ames, Iowa

[73] Assignee: Iowa State University Research Foundation, Inc., Ames, Iowa

[22] Filed: Dec. 10, 1971

[21] Appl. No.: 206,667

[52] U.S. Cl. .................. 310/9.5; 310/8; 310/9.8; 310/8.1; 333/30 R; 73/67.5 R
[51] Int. Cl.² .......................................... H01L 41/04
[58] Field of Search ............ 310/8.1, 9.7, 9.8, 9.5, 310/9.6, 8.2, 8.3; 333/30 R; 73/67, 70, 67.5, 67.6

[56] References Cited
UNITED STATES PATENTS

| | | | |
|---|---|---|---|
| 2,587,414 | 2/1952 | Valkenburg et al. | 333/30 R |
| 2,921,134 | 1/1960 | Greenspan et al. | 333/30 R |
| 3,343,105 | 9/1967 | Van Der Pauw | 310/9.7 X |
| 3,360,749 | 12/1967 | Sittig | 333/30 R |
| 3,400,340 | 9/1968 | Papadakas | 310/8.2 X |
| 3,512,400 | 5/1970 | Lynnworth | 73/67.5 R |
| 3,518,582 | 6/1970 | Pizzarello | 310/8.1 X |
| 3,611,203 | 10/1971 | Cooper | 333/30 R |

OTHER PUBLICATIONS
Surface Elastic Waves, by R.M. White, Proceedings of IEEE Vol. 58, No. 8, Aug. 1970, pp. 1238–1276.

*Primary Examiner*—Mark O. Budd
*Attorney, Agent, or Firm*—Dawson, Tilton, Fallon & Lungmus

[57] ABSTRACT

A device for generating or sensing transverse elastic bulk waves in solids includes a piezoelectric material engaging a surface of the solid and having a two-fold axis or equivalent symmetry extending parallel to the surface of the solid. A pair of electrodes are located on a surface of the transducer extending perpendicular to the surface of the solid which the material contacts. Each electrode has one or more conductive fingers elongated in a direction parallel to the two-fold axis of the material. The fingers of the electrodes are interlaced. When used as a generator of bulk waves, a source of alternating voltage excites the electrodes. The electrodes thus generate deep surface waves in the piezoelectric material which are transformed into bulk waves in the test solid. Similarly, bulk waves in the test solid are transformed into deep surface waves in the piezoelectric material which may then be sensed by the electrodes.

10 Claims, 6 Drawing Figures

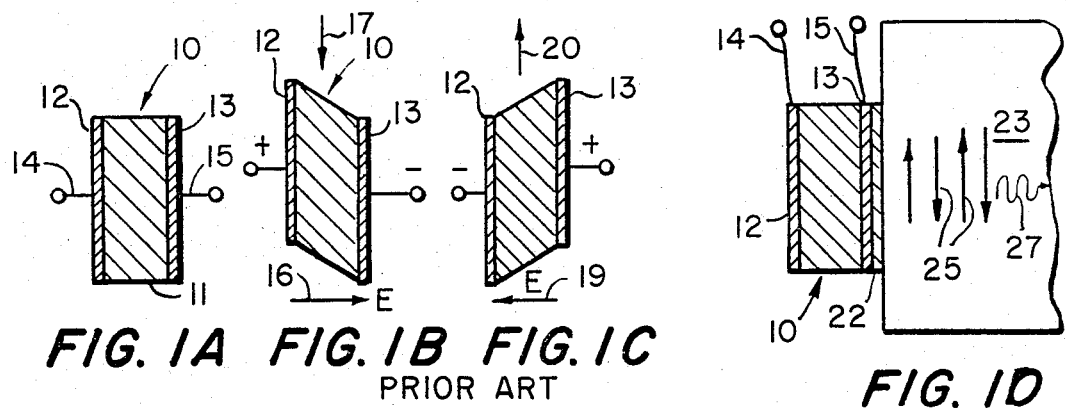
FIG. 1A  FIG. 1B  FIG. 1C
PRIOR ART
FIG. 1D
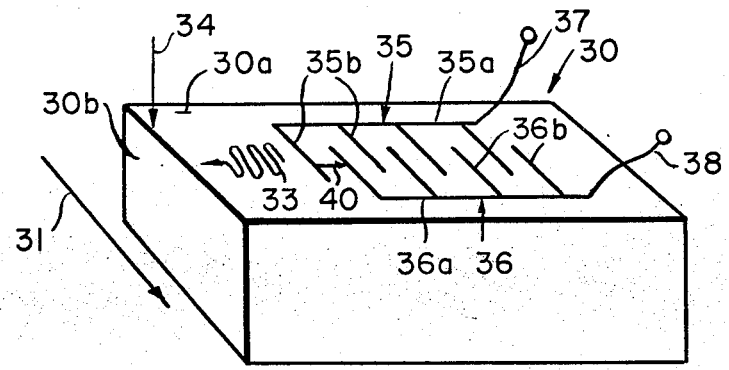
FIG. 2
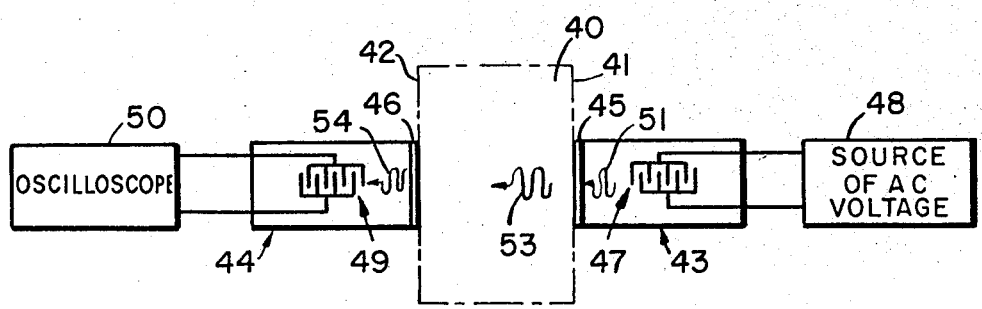
FIG. 3
INVENTORS
Clifford K. Day
George G. Koerber
BY *James J. Hill*
ATTORNEY

SYSTEM FOR GENERATING OR SENSING TRANSVERSE ELASTIC BULK WAVES IN SOLIDS

BACKGROUND AND SUMMARY

The present invention relates to a system for generating or sensing transverse elastic bulk waves in solids. One of the principal uses of bulk waves in solids is the detection and isolation of fractures or other faults in the solid material, as in non-destructive testing of materials. Such testing is of prime importance in the field of atomic energy, and even more particularly, in the construction and operational testing of nuclear reactors.

In non-destructive testing, an elastic bulk wave is transmitted through the solid being tested, and the transmission characteristics are monitored either at a remote location or upon reflection of the wave. Various signal processing techniques are then used on the sensed signal to determine whether the bulk wave has passed through a faultless solid or, alternatively, whether there exists a fault somewhere in the solid.

A transverse bulk wave in a solid material is characterized by an oscillatory motion of particles in the solid perpendicular to the direction of propagation of the wave (i.e., in the shear plane) within the material; and this characteristic is due to the inherent elastic nature, within limits, of solid matter. Thus, the waves are sometimes referred to as bulk shear waves.

As will be explained in more detail within, heretofore bulk waves have been generated by means of a piezoelectric transducer having a sandwich-type construction with the piezoelectric material in the center and conductive electrode pads fixed to opposite surfaces of the substrate. Bulk waves are generated within the piezoelectric substrate by applying an alternating voltage to the two surface electrodes. These bulk waves are then coupled from the substrate through one of the surface electrodes into the solid material being tested. Similarly, bulk waves are sensed by bonding one of the electrodes to the material under test to transmit bulk waves from the material into the piezoelectric substrate. The bulk waves in the piezoelectric substrate are then sensed at the electrodes.

Piezoelectric materials have long been known in the art, and they are characterized in that if an electric field is applied to the material, it will tend to distort; and conversely, if a stress is applied to the material, an electric field will be generated. In piezoelectric materials used for bulk shear wave generation when an electric field is applied, the material distorts in a plane perpendicular to the field vector.

The present invention makes use of a piezoelectric material which is characterized in that it has a two-fold axis or equivalent symmetry—that is, it includes any combination of symmetry elements in which a two-fold axis of symmetry exists. A pair of electrodes are formed on a surface of the substrate which is parallel to the two-fold axis; and each electrode preferably takes the form of a plurality of elongated, interconnected conductive fingers which are also parallel to the two-fold axis. The conductive fingers of each electrode are interlaced to form a pair of interdigital electrodes.

The substrate is preferably bonded to the material being tested along one side which is parallel to the two-fold axis and perpendicular to the surface on which the interdigital electrodes are formed. When used as a generator of bulk shear waves, an alternating voltage source is connected to the electrodes to apply an alternating electric field in the material transverse of the two-fold axis; and this generates surface waves which propagate along the surface on which the electrodes are formed and perpendicular to the two-fold axis of the crystal. Normally, surface waves excited in a solid decay very rapidly with depth, and they can be said to be truly confined to the surface. However, with the piezoelectric material having a two-fold axis, we have found the decay of surface waves with depth may be very much less such that they are almost indistinguishable from bulk waves, as will be more fully explained below. We call such waves as are generated according to our invention deep surface waves because of the relatively small attenuation of the surface waves. Without so limiting our invention, we postulate that it is this characteristic which facilitates transformation of surface waves on the transducer to and from bulk waves in a solid. These surface waves are thus transformed to the material under test as bulk shear waves. Whether used as a sensor or generator of bulk shear waves, the orientation of the transducer relative to the material being tested and the formation of electrodes on the transducer is the same. That is, bulk waves in the material tested are coupled out of a surface perpendicular to the surface of the transducer on which the electrodes are formed and parallel to the two-fold axis. Corresponding waves in the transducer then form deep surface waves which may be sensed by the interdigital electrode configuration.

The transducer of the present invention, by eliminating the metallic electrode interposed between the solid material under test and the piezoelectric material, as required in prior devices, yields a system which is more sensitive and more efficient than prior transducers because the interposed metallic surface of prior devices is usually acoustically different than either the piezoelectric material or the solid material under test, and it therefore produces reflections at the interfaces. Further, as will be explained in greater detail below, the present device is capable of operating at a much higher frequency of operation than are the prior devices. This is due principally to the fact that the operating frequency of the inventive transducer is dependent upon the design of the interdigital electrodes, but is independent of the thickness of the piezoelectric material. That is, the operating frequency of prior devices is determined by the thickness of the material between the two electrodes; whereas the operating frequency of the present device is independent of the thickness of the piezoelectric substrate.

Further, the present system affords greater operational flexibility because the bandwidth can be varied by electrode design, as will be explained more completely below. Another advantage of the present invention is that the fabrication of the transducer is greatly simplified, using well-developed techniques in deposition of metals to form the interdigital electrode, and the device is simply bonded or placed in intimate engaging contact with the surface of the material being tested with a suitable adhesive or fixture. The device of the present invention may be used in all systems wherein elastic bulk shear waves are generated or monitored.

Other features and advantages of the present invention will be apparent to persons skilled in the art from the following detailed description of a preferred embodiment accompanied by the attached drawing wherein identical reference numerals will refer to like parts in the various views.

THE DRAWING

FIGS. 1A–1D illustrate the generation of bulk shear waves according to the prior art;

FIG. 2 is a perspective view of a transducer according to the present invention; and FIG. 3 is a functional block diagram of a system for generating and receiving bulk waves in a material according to the present invention.

DETAILED DESCRIPTION

Referring to FIGS. 1A–1D, there is shown a conventional device for generating or sensing bulk shear waves. In FIG. 1A, a transducer is generally designated by reference numeral 10, and it includes a central piezoelectric substrate 11, opposite surfaces of which are provided with conductive electrodes designated 12 and 13. The substrate 11 is normally a single crystal. Attached to the electrodes 12, 13 are conductive wires 14 and 15 respectively for transmitting electrical signals to or from the transducer.

When an electric field is applied to the transducer 10, in the polarity shown in FIG. 1B, the electric field vector extends in the direction of the arrow 16 from the electrode 12 to the electrode 13; and the piezoelectric crystal 11 experiences a shear strain in the plane indicated by the arrow 17 extending perpendicular to the plane of the page of FIG. 1B, thus causing the electrodes 12, 13 to be displaced vertically relative to each other as illustrated in the drawing, although the displacement shown is greatly exaggerated.

If the polarity of the applied field is reversed so that the electric field vector E extends in the direction of the arrow 19 in FIG. 1C, a similar but opposite shear stress indicated by the arrow 20 is induced in the crystalline substrate to reverse the relative displacement of electrodes 12, 13.

Turning now to FIG. 1D, if the transducer 10 is bonded by means of an agent 22 to a solid material 23, and an alternating voltage applied to the conductors 14, 15, bulk waves will be generated in the substrate 11, and they will be transmitted through the electrode 13 and the bonding material 22 and into the material under test 23. The direction of particle motion within the material 23 is in the direction of the arrows 25—that is, an individual particle oscillates in a vertical direction. The waves are propagated, however, from left to right, as diagrammatically illustrated by the serpentine arrow 27.

The efficiency with which transducers of the type illustrated in FIG. 1A are capable of generating bulk shear waves in a solid object is dependent upon the frequency of the applied voltage, the dimensions of the crystalline substrate, the thickness and acoustic impedance of the metallic electrode 13, the thickness and acoustic impedance of the bonding material 22, and the acoustic match or mismatch between the crystalline substrate 11 and the solid material 23 under test. The upper limit on the frequency of operation of the transducer 10 is determined by the thickness of the crystalline substrate 11. For example, if it is desired to generate a bulk wave having a frequency of 2 megahertz, the thickness of the crystalline substrate 11 would be of the order of 10 mils.

Turning now to FIG. 2, there is shown a transducer constructed according to the present invention. Reference numeral 30 generally designates a rectilinear block or piece of piezoelectric material which has the characteristic that it will support and transmit surface waves in which the oscillatory particle motion is transverse to the direction of propagation and parallel to the surface. Surface waves of this type are often called SH (for Shear, Horizontally polarized) surface waves. The existence of a two-fold axis of symmetry in the piezoelectric material is a necessary condition for the existence of an SH surface wave mode. It is also necessary that this two-fold axis be oriented relative to the surface and the direction of propagation as disclosed above.

The two-fold axis for the piezoelectric material 30 is designated by the arrow 31. SH surface waves are similar to shear bulk waves in that the particle motion is transverse to the direction of propagation of the wave; however, surface waves differ from bulk shear waves in that the amplitude of particle oscillation decays, or is damped along a direction perpendicular to the surface in which the wave exists. Normally, this damping is very large as a function of depth. However, we have found that under circumstances disclosed below, the damping is less pronounced; and we believe, without intending to limit our invention, that it is this characteristic of reduced damping of surfaces as they propagate into the body of the substrate which permits the transformation into bulk shear waves in the material being tested which we have observed and which is an important feature of the present invention. The invention, therefore, will work with piezoelectric materials which have a two-fold axis of symmetry at least—i.e., it will also work with materials having a four-fold or six-fold axes.

In order to delineate the circumstances under which reduced damping or slow decay of the surface wave as a function of depth occurs, it will be helpful to define two classes of piezoelectric materials.

Class I consists of single crystalline materials having 6mm, 4mm, 6, or 4 symmetry and the poled piezoelectric ceramics. In all materials in this category, the damping is directly proportional to the piezoelectric coupling constant, and is inversely proportional to $(1 + k)$ where $k$ is the relative dielectric permittivity of the material. It is noted that a poled piezoelectric ceramic has structural features that provide a two-fold axis of symmetry parallel to the poling direction.

Class II consists of all piezoelectric materials not in class I, and which have a two-fold axis of symmetry. In such materials, a surface wave can only exist for a limited range of angular orientations of the surface about the two-fold axis. Near the limits of the range of existence of the surface wave, it invariably decays very slowly. The invention therefore contemplates the use of materials in Class II if the surface is appropriately oriented.

It should be noted that a two-fold axis of symmetry is provided by other elements of symmetry; that is, a 4-, 6-, or 4-fold rotation inversion axis, or planes of symmetry intersecting at dihedral angles of 90°, 45°, or 30° provide a two-fold axis of symmetry. It will thus be appreciated that various piezoelectric materials, including ceramics as well as crystals are useful in practicing the invention as long as the material exhibits a two-fold axis of symmetry.

Referring now to the substrate 30, if a surface wave is generated in the surface 30a of the block 30, and propagated along the direction of the serpentine arrow 33, the particulate motion being everywhere parallel to the two-fold axis 31, the wave will propagate along the surface 30a, but it will also propagate in a direction perpendicular to the surface 30a, as indicated by the arrow 34. A pair of electrodes 35, 36 are attached to the surface 30a of the substrate 30. The electrode 35 includes a base conductor 35a from which a plurality of finger conductors 35b extends. The finger conductors 35b, it will be observed, extend parallel to the two-fold axis 31. Similarly, the electrode 36 includes a base conductor 36a and a plurality of finger conductors 36b. The finger conductors 36b are parallel to the finger conductors 35b, and the sets of finger conductors 35b, 36b are alternately located or interlaced. Thus, the electrodes 35, 36 are referred to as interdigital electrodes.

Connected to the base line 35a of the electrode 35 is a conductor 37, and a similar conductor 38 is connected to the base line 36a. A source of alternating voltage (not shown) is connected to the conductors 37, 38. When the interdigital electrodes are energized by the ac voltage source, it will be observed that the electric field intensity vector between adjacent ones of the finger electrodes, designated by the arrow 40 extends along the surface 30a of the substrate and in a direction perpendicular to the two-fold axis 31. As the field alternates, the orientation of the vector 40, of course, reverses direction. The application of the electric field by means of the interdigital electrodes generates a piezoelectric stress in a plane parallel to the surface 30b of the block 30, and the surface wave, as mentioned, propagates perpendicular to the plane of the surface 30b. At the same time, the wave generated at the surface 30a propagates down into the substrate parallel to the arrow 34. The rate of decay of this latter wave is small for ceramic piezoelectric materials having a two-fold axis. It is this wave which we call a deep surface wave.

Similarly, if a surface wave is propagated in the surface 30a of the block 30, in a direction perpendicular to the two-fold axis 31, it will be sensed by the interdigital electrodes 35, 36 so as to generate an electric potential difference between these electrodes which may then be sensed. One type of piezoelectric material which we have found suitable for generating surface waves of the type described is a lead-zirconate-titanate ceramic piezoelectric material sold under the designation PZT-5 and manufactured by Clevite Corporation of Cleveland, Ohio. This type of material is also known to be useful in fabricating a delay line wherein a pair of interdigital electrodes similar to the ones disclosed generates a surface wave which propagates along the material and is sensed at a remote location on the same substrate by a similar pair of interdigital electrodes. The spacing between the sets of electrodes and the propagation velocity of the surface wave determines the delay time, and such a delay device is known to be used in radar systems for signal processing applications.

Turning now to FIG. 3, there is shown in schematic form, a test which we have conducted to demonstrate that surface waves generated in a transducer of this type can be transformed to bulk waves in a solid and conversely that bulk waves in a solid can be transformed to surface waves and sensed in the transducer. The material under test is a three-dimensional shape schematically designated by the chain line 40, and including two surfaces designated 41 and 42 to which transducers 43 and 44 (similar to the transducers disclosed above and illustrated in FIG. 2) are respectively secured. The transducers 43 and 44 may be attached by means of bonding layers designated 45 and 46 respectively. The bonding material may be epoxy resin. Alternatively, the transducer and material may simply be placed in close engagement, as with a fixture. The transducer 43 includes a set of interdigital electrodes generally designated by reference numeral 47 which are excited by a source of ac voltage 48. The transducer 44 includes a pair of interdigital electrodes 49 which are coupled to an oscilloscope 50.

When the interdigital electrodes 47 are excited, a surface wave schematically illustrated by the serpentine arrow 51 is generated in the upper surface of the transducer 43, and it is propagated in a direction perpendicular to the poled axis of the substrate through the epoxy layer 45 into the material being tested. The surface wave then is transformed into a bulk shear wave in the solid material apparently because as a surface wave in the transducer, it has little amplitude attenuation with depth as contrasted with normal surface waves so as to be almost indistinguishable from a bulk wave in the transducer when generated according to the method discussed in connection with FIGS. 1A–1C. The bulk wave in the solid being tested, which in this case was an aluminum bar 4 inches long, is propagated as schematically indicated by the serpentine arrow 53. The bulk shear wave is then coupled out of the surface 42 of the material 40, through the epoxy layer 46 and into the second transducer 44 as a surface wave indicated by the serpentine arrow 54 where the interdigital electrodes 49 sense it, and the resultant electrical signal may be displayed on an oscilloscope 50.

In materials of Class I as defined herein which include piezoelectric ceramics, the wave will decay to $1/e$ of its surface amplitude in a distance or depth, D, into the material in the direction of arrow 34 as given by the following equation:

$$D = \frac{1+K^2}{K^2} (1+k) \frac{\lambda}{2\pi} \text{ meters} \quad (1)$$

where $\lambda$ is the wavelength, $k$ is the relative permittivity of the substrate, and $K$ is the coupling constant. $K^2$ is defined by $$K^2 = e^2/\epsilon_o k C$$

in which $e$ is the piezoelectric constant, $\epsilon_o$ is the permittivity of free space, $k$ is the relative permittivity, and $C$ is the shear stiffness of the material.

It will be seen from the above relationships that the penetration depth of the surface waves into the transducer substrate will be enhanced with a relatively large relative permittivity, $k$, or a relatively low coupling constant, $K$. As already mentioned, we postulate that this relatively unattenuated penetration of surface waves into the body of the substrate, so as to simulate bulk shear waves in the substrate, greatly facilitates transformation of bulk shear waves to and from the test material.

In our experiment, this depth was about 1 meter, whereas the thickness of the substrate was only about 1 cm. and thus there was relatively little attenuation of the surface wave. That is, the surface wave appeared for all practical purposes as bulk shear wave in the transducer. It will be observed from Equation (1) above that the penetration depth of the wave increases with wavelength, (i.e. it decreases with frequency), and increases with relative permittivity, but decreases with $K^2$. Typical values of $K^2$ range from about 0.01 to 0.6 in practical piezoelectric materials. The relative permittivity will normally lie in the range 10 – 100, but in ferroelectric ceramics, it will range from 1000 to 5000. The decay formula will differ for crystals of different symmetry, but the general trends described above will probably pertain. Equation (1) applies to Class I crystals or ceramics.

The following is an example of the decay depth for a surface wave in a Class I material, PZT-5, having a wavelength of $10^{-3}$ meters:

$$D = \frac{1.6}{.6} \times \frac{2000}{} \times \frac{10^{-3}}{2\pi} 0.85 \text{ meters}$$

Examples of Class II materials for which decay depths have been calculated are the 45° cut on Bismuth Germanium Oxide in which D is approximately 560 wavelengths and Barium Sodium Niobate in which D is approximately 3000 to 5000 wavelengths. There is no single formula for calculating decay for all Class II materials.

With an arrangement such as that shown in FIG. 3, we have demonstrated the operability of the use of a transducer of the type illustrated in FIG. 2 both as a generator of deep surface waves which are then converted to bulk shear waves and as a receiver of bulk shear waves which are converted to deep surface waves. We thus have discovered a method of transmitting bulk shear waves in solids which has certain advantages over the prior methods of and devices for generating bulk shear waves. One advantage is that there is no need for the interposition of a metallic electrode between the transducer and the solid material being tested, such as the metallic electrode 13 shown in FIG. 1D. Such an electrode, being made of metal, has introduced acoustical mismatches and reflections, thereby reducing the efficiency with which mechanical energy may be transferred from the transducer to the bulk material.

Secondly, with a configuration of interdigital electrodes disclosed, our transducer can operate at a much higher frequency. The frequency of operation of the inventive transducer depends on the spacing of the fingers of the electrodes. The center-to-center spacing of the electrodes determines the operating frequency of the device. That is, the center-to-center spacing is one-half the wave length of the operating frequency. Thus, if the center-to-center spacing of adjacent finger electrodes is reduced, the operating frequency increases; and with known fabrication techniques, operation of up to 2.5 gigahertz is feasible. This is an improvement of at least two orders of magnitude over present operating devices.

Further, the frequency bandwidth of the transducer of the present invention is dependent upon the center-to-center spacing of adjacent finger electrodes and the number of electrodes such that the bandwidth (as determined by the 3db. cutoff frequencies), $\Delta f$ as given by the following expression:

$$\Delta f = \frac{2}{n} f_c$$

where:

$n$ is the number of electrode fingers on each electrode and $f_c$ is the center frequency of the device.

The ability to determine the bandwidth of the device may have significant advantages in certain applications, for example, in the sensing and filtering of acoustic emissions in nuclear reactors wherein a known or predetermined acoustic emission may be representative of a failure in the piping system or pressure vessel of a reactor. By "tuning" the transducer itself to the desired acoustic emission, electronic signal processing of the sensed acoustic energy may be significantly reduced or eliminated. Further, frequency ranges heretofore prohibited may be investigated with the use of the present invention.

Having thus described in detail the preferred embodiment of the invention, persons skilled in the art will be able to modify certain of the structure which has been disclosed and to substitute equivalent elements for those given while continuing to practice the principle of the invention; and it is, therefore, intended that all such modifications and substitutions be covered as they are embraced within the spirit and scope of the appended claims.

We claim:

1. In combination, a solid test material for supporting bulk shear waves and having an exterior surface; a transducer of piezoelectric material having at least a two-fold axis of symmetry and first and second intersecting surfaces parallel to said two-fold axis; said first surface of said transducer coupled to said exterior surface of said test material; electrode means on said second surface of said transducer; and source means for exciting said electrode means to generate a transverse surface wave on said second surface of said transducer and propagating in a direction perpendicular to said two-fold axis, said surface wave also extending into the body of said transducer and propagating toward said first surface as a deep surface wave characterized in that its intensity will attenuate to $1/e$ of its surface intensity value at a distance substantially greater than the thickness of said transducer along a direction perpendicular to said first surface.

2. The system of claim 1 wherein said electrode means comprise at least one pair of electrodes, each including an elongated conductive member extending parallel to said two-fold axis of said material and overlapping each other when viewed in the direction of wave propagating, whereby when said electrodes are excited by a source of electric potential, an electric field vector will extend perpendicular to said two-fold axis.

3. The system of claim 2 wherein each one of said pair of electrodes includes a plurality of conductive fingers extending parallel to said two-fold axis on said other surfaces of said substrate material; said fingers of one of said electrodes being interlaced with the fingers of the other of said electrodes, said combination further comprising a source of alternating voltage for exciting said electrodes to generate a surface wave in said other surface of said substrate material, said surface wave being transmitted into said test material as a bulk wave.

4. The system of claim 2 wherein each of said pair of electrodes includes a plurality of parallel conductive fingers extending parallel to said two-fold axis, said fingers of one of said electrodes being interlaced with the fingers of the other of said electrodes, said piezoelectric material being adapted to receive bulk waves transmitted through said test material and transforming said bulk waves as deep surface waves in said transducer and in a direction perpendicular to said two-fold axis, whereby said electrodes will sense said deep surface waves and generate electrical signals representative thereof.

5. In combination, a body of material having a surface and adapted to support bulk shear waves; and a transducer for generating bulk shear waves in said material including a piezoelectric substrate characterized in having at least a two-fold axis of symmetry, said substrate having a first surface parallel to said axis and a second surface contiguous with and intersecting said first surface and parallel to said axis, said second surface of said substrate being coupled to said surface of said material, electrode means on said first surface of said transducer for generating an alternating electric field in said first surface of said substrate, the electric field vectors of said field extending perpendicular to said two-fold axis of said substrate for generating surface waves in said second surface of said substrate, said surface waves being transmitted through said substrate as deep surface waves characterized in that their intensity will attenuate to $1/e$ of their surface intensity value at a distance substantially greater than the thickness of said transducer along a direction perpendicular to said second surface and being transformed into bulk shear waves in said test material.

6. The combination of claim 5 wherein said substrate has a relatively high relative permittivity and piezoelectric constant.

7. The combination of claim 5 wherein said substrate is a lead-zirconate-titanate ceramic piezoelectric material.

8. In combination, a test material defining a surface and adapted to support bulk shear waves; and a transducer including a substrate of piezoelectric material having a two-fold axis of symmetry and having first and second intersecting surfaces contiguous with each other and parallel to said two-fold axis, said second surface being coupled to said surface of said material, and said first surface extending outwardly of said material, electrode means on said first surface of said transducer adapted to sense bulk waves transmitted from said material and converted to deep surface waves in said substrate propagating in a direction perpendicular to said two-fold axis, said deep surface waves in said transducer being characterized in that their intensity will attenuate to $1/e$ of their surface intensity value at a distance substantially greater than the thickness of said transducer along a direction perpendicular to the surface on which said electrodes are mounted.

9. The combination of claim 8 wherein said substrate is a lead-zirconate-titanate ceramic piezoelectric crystal.

10. The combination of claim 8 wherein said substrate has a relatively high permittivity and piezoelectric constant.

* * * * *